United States Patent [19]

Shapiro et al.

[11] Patent Number: 5,795,342

[45] Date of Patent: Aug. 18, 1998

[54] OCULAR IRRIGATION DEVICE

[75] Inventors: Michael B. Shapiro, Madison; Michael L. Kvalo, Portage, both of Wis.

[73] Assignee: Eye-Deal Ocular Safety Products, Inc., Madison, Wis.

[21] Appl. No.: 691,271

[22] Filed: Aug. 2, 1996

Related U.S. Application Data

[63] Continuation-in-part of Ser. No. 589,295, Jan. 22, 1996, abandoned.

[51] Int. Cl.$^6$ .................................................. A61M 35/00
[52] U.S. Cl. .................................................. 604/300; 604/294
[58] Field of Search .................................. 604/294–302

[56] References Cited

U.S. PATENT DOCUMENTS

| Re. 28,873 | 6/1976 | Morgan | 128/249 |
|---|---|---|---|
| 3,664,340 | 5/1972 | Morgan | 128/249 |
| 4,543,096 | 9/1985 | Keene | 604/300 |
| 4,623,337 | 11/1986 | Maurice | 604/298 |
| 4,792,334 | 12/1988 | Py | 604/301 |
| 4,798,599 | 1/1989 | Thomas | 604/290 |
| 4,921,477 | 5/1990 | Davis | 604/22 |
| 4,946,452 | 8/1990 | Py | 604/301 |
| 4,963,693 | 10/1990 | Kodl | 174/11 R |
| 5,030,214 | 7/1991 | Spector | 604/301 |
| 5,171,307 | 12/1992 | Sanning | 661/327 |
| 5,207,659 | 5/1993 | Pennaneac'h et al. | 604/298 |
| 5,328,456 | 7/1994 | Horiguchi et al. | 604/22 |
| 5,360,398 | 11/1994 | Grieshaber et al. | 604/30 |
| 5,366,448 | 11/1994 | Basilice et al. | 604/290 |
| 5,387,201 | 2/1995 | Fowler | 604/290 |

FOREIGN PATENT DOCUMENTS

WO 93/19806 10/1993 WIPO.
WO 93/20785 10/1993 WIPO.

Primary Examiner—John G. Weiss
Assistant Examiner—Ki Yong O
Attorney, Agent, or Firm—Michael, Best & Friedrich LLP

[57] ABSTRACT

An ocular irrigation device including an engaging member engageable with an eyelid to hold the eyelid open, a source of fluid, and a fluid dispenser operatively associated with the source of fluid and slidably connected to the engaging member. The fluid dispenser is arcuately-shaped and has a plurality of fluid-dispensing orifices positionable under an eyelid to provide fluid directly under the eyelid at multiple arcuately-spaced locations. The engaging member includes a wire formed into an arcuate portion that is positionable under an eyelid. The fluid dispenser is positionable in spaced relation relative to the engaging member such that the engaging member can engage and hold one eyelid open and the fluid dispenser can engage and hold the opposing eyelid open. The fluid dispenser includes an opening for allowing visual and/or physical access to the eye when the orifice is positioned under the eyelid. The sliding member can include raised portions for improving frictional engagement with the sliding member.

11 Claims, 2 Drawing Sheets

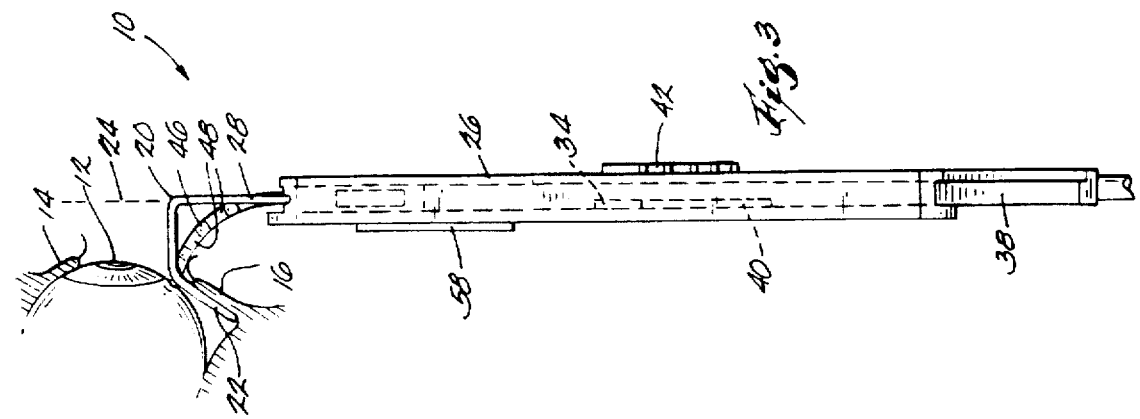

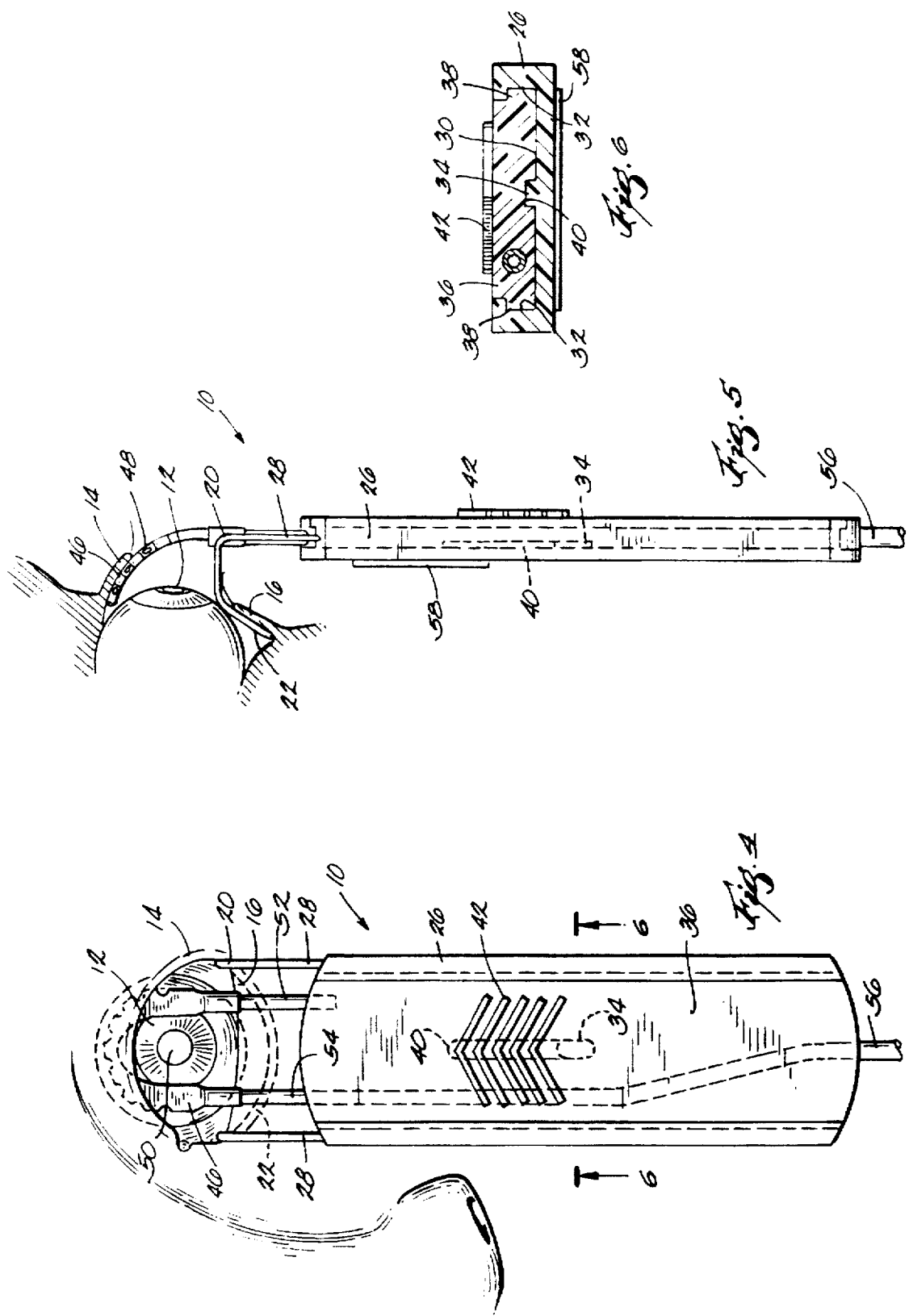

OCULAR IRRIGATION DEVICE

This is a continuation-in-part of application Ser. No. 08/589,295, filed Jan. 22, 1996, entitled "OCULAR IRRIGATION DEVICE", now abandoned.

FIELD OF THE INVENTION

The present invention generally relates to ocular medical devices and, more particularly, to ocular irrigation devices for flushing foreign material from an eye.

BACKGROUND OF THE INVENTION

Injuries to the eye caused by contact with foreign material (e.g., chemicals) can cause patient discomfort, temporary disability, and even blindness. In a workplace environment, these injuries can result in lost productivity, workers compensation costs, and potential liability.

To alleviate these problems, it is advantageous to remove the foreign material from the eye as soon as possible. Immediate removal of the foreign material after an accident can mean the difference between a full recovery of vision and a life of blindness with chronic pain and photophobia. One technique for removing the foreign material is to thoroughly irrigate the eye with solution, such as saline. Traditionally, this has been accomplished by manual washing with a stream of solution, such as from a bottle or IV tubing. In order to irrigate the whole eye, the person administering the irrigation must hold the patient's eyelids open while irrigating. This technique is very time and labor intensive, particularly when both eyes are contaminated.

Many workplace facilities include ocular irrigation stations where a patient can position his head adjacent a solution dispenser and provide a stream of solution from the dispenser to the eye. One problem with such irrigation stations is that the patient must be alert enough to go to the station and use it properly. In addition, proper positioning of the eye relative to the dispenser can be a problem, particularly when the patient is in pain or temporarily blinded. Further, such stations are not mobile, and therefore cannot be transported to an accident site for use on an incapacitated patient.

U.S. Pat. No. 3,664,340 discloses a scleral lens having an attached tube for introduction of fluid to the eye. The scleral lens is positioned to completely cover the inside surface of the eyelids. Fluid, such as medication, is provided to the eye through the attached tube. This device is portable, and therefore can provide fluid to the eye of an incapacitated person.

SUMMARY OF THE INVENTION

One problem with the above-described design is that it is difficult to insert the lens into the eye because the upper eyelid must be lifted far away from the injured eye, thereby requiring another hand. This task is particularly difficult when the patient is in a state of panic and intense pain. In addition, the fluid port is directed only at the cornea, thereby only irrigating a single area of the eye and potentially damaging the corneal epithelium. Further, the closed lens design does not adequately flush the inner surfaces of the eyelids, and inhibits escape of the foreign material, resulting in prolonged contact of the foreign material with the eye and eyelids.

The present invention alleviates the above-noted problems by providing an ocular irrigation system that incorporates an irrigation device with an improved eyelid speculum.

The present invention allows the speculum to be quickly and easily engaged with the lower eyelid and slid under the upper eyelid with a single hand. In addition, the solution is provided directly under at least one of the eyelids at multiple locations to provide adequate irrigation to the eye and under the surface of the eyelids. Further, irrigation is provided from the periphery of the eye, rather than directly at the cornea, thereby inhibiting damage to the corneal epithelium.

In one aspect, the present invention provides an ocular irrigation device including an engaging member engageable with an eyelid to hold the eyelid open, a source of fluid, and a fluid dispenser operatively associated with the source of fluid and connected to the engaging member. The fluid dispenser has at least one fluid-dispensing orifice positionable under an eyelid to provide fluid directly under the eyelid. Preferably, the engaging member includes a wire (e.g., having a round cross section) formed into an arcuate portion that is positionable under an eyelid. The use of a wire decreases the surface area that is covered by the engaging device, thereby enhancing irrigation and moisturization under the eyelid.

The fluid dispenser is preferably positionable in spaced relation relative to the engaging member such that the engaging member can engage and hold one eyelid open and the fluid dispenser can engage and hold the opposing eyelid open. Such a design allows adequate drainage of foreign material away from the eye. The fluid dispenser can include a hollow tubular member with the orifice positioned in the tubular member. Further, the fluid dispenser can include an opening for allowing visual and/or physical access to the eye when the orifice is positioned under the eyelid. An adhesive patch facilitates securement of the dispenser to a patient's face.

In another aspect, the present invention provides an ocular irrigation device having a source of fluid and a fluid dispenser operatively associated with the source of fluid. The fluid dispenser includes an arcuate portion positionable under an eyelid, the arcuate portion including at least one orifice for dispensing fluid under the eyelid. In one embodiment, the arcuate portion includes a plurality of orifices capable of dispensing fluid under the eyelid at multiple arcuately-spaced locations. Preferably, the device further includes an engaging member connected to the fluid dispenser and engageable with an opposing eyelid. The engaging member and the fluid dispenser are capable of cooperatively holding the eyelid and the opposing eyelid separated.

In yet another aspect, the present invention provides an ocular irrigation device having an engaging member engageable with an eyelid to hold the eyelid open, a source of fluid, and a fluid dispenser operatively associated with the source of fluid and linearly slidably connected to the engaging member. For example, the device can further include a base member supporting the engaging member, and a sliding member supporting the fluid dispenser and linearly slidably engaging the base member. The base member preferably includes a channel, and the sliding member is at least partially positioned within the channel. The sliding member can include means for improving frictional engagement with the sliding member, such as raised portions extending upwardly from the sliding member.

The present invention also provides a method of separating two opposing eyelids using a device having a first member and a second member slidable relative to the first member. The method includes the steps of engaging the first member with one of the eyelids, linearly sliding the second member relative to the first member toward the opposing eyelid, engaging the second member with the opposing eyelid, and positioning the second member in spaced relation relative to the first member such that the first and second members cooperatively hold the eyelids separated. If desired, the method can further include the step of providing fluid under at least one of the eyelids. For example, the step of providing fluid can include discharging fluid through at least one of the first and second members.

BRIEF DESCRIPTION OF THE DRAWINGS

FIG. 1 is a perspective view of an ocular irrigation device embodying the present invention.

FIG. 2 is a front view of the device illustrated in FIG. 1, with the sliding member in the retracted position.

FIG. 3 is a side view of the device illustrated in FIG. 1 in partial section, with the sliding member in the retracted position.

FIG. 4 is a front view of the device illustrated in FIG. 1, with the sliding member in the extended position.

FIG. 5 is a side view of the device illustrated in FIG. 1 in partial section, with the sliding member in the extended position.

FIG. 6 is a section view taken along line 6—6 in FIG. 4.

DETAILED DESCRIPTION

FIGS. 1–6 illustrate an ocular irrigation device 10 embodying the present invention. The device 10 is preferably used to irrigate an eye 12 and to hold the upper eyelid 14 and the lower eyelid 16 open, as described below in more detail.

The device 10 generally includes an engaging member 20 designed to engage an eyelid. In the illustrated embodiment, the engaging member 20 comprises a wire having an arcuate portion 22 that can be positioned under the lower eyelid 16, as illustrated in FIG. 3. When viewed from the side (FIG. 3), the illustrated arcuate portion 22 is positioned at an angle of about 36.0° relative to a reference plane 24 defined by a base member 26. The illustrated wire has a round cross section with a diameter of about 0.8 mm, and is made from teflon coated stainless steel. The engaging member 20 further includes end portions 28 (FIGS. 1 and 2) that are connected to the base member 26 at two spaced locations. The end portions 28 can be molded into the base member 26 or, alternatively, can be connected to the base member 26 after the base member 26 is formed, such as by bonding the end portions 28 into holes in the base member 26. In the illustrated embodiment, the base member 26 is made of plastic. The base member 26 includes a longitudinally-extending channel 30 with undercuts 32 in the sides of the channel 30, and a raised tab 34 extending upwardly from the base member 26. The channel 30 defines the above-mentioned reference plane 24.

A sliding member 36 is slidably positioned within the channel 30 of the base member 26. The sliding member 36 includes side ledges 38 that fit within the undercuts 32 to hold the sliding member 36 in place within the channel 30. The sliding member 36 further includes a longitudinally-extending slot 40 that slidably receives the tab 34 of the base member 26, thereby limiting the range of sliding motion between the sliding member 36 and the base member 26. A plurality of raised portions or ribs 42 are provided on the top surface of the sliding member 36 to enhance the frictional engagement of a user's hand with the sliding member 36, thereby facilitating manual manipulation of the sliding member 36 relative to the base member 26. The sliding member 36 is linearly slidable relative to the base member 26 between a retracted position (FIGS. 2 and 3) and an extended position (FIGS. 4 and 5). The sliding interconnection between the sliding member 36 and the base member 26 is preferably designed to provide some resistance to movement so that the sliding member 36 will stay in place relative to the base member 26 unless acted upon by the user of the device 10.

A fluid dispenser 44 is connected to the sliding member 36 to facilitate discharge of fluid into the eye 12. The illustrated fluid dispenser 44 includes a hollow arcuate member 46 that has a plurality of arcuately-spaced orifices 48 in an outer wall thereof. The orifices 48 provide communication between the interior and the exterior of the arcuate member 46. The illustrated arcuate member 46 is made of clear hygroscopic tubing. The arcuate member 46 includes an opening 50 in a mid-portion thereof. The opening 50 facilitates viewing of the eye 12 when the device 10 is in used, as described below in more detail. The arcuate member 46 is connected to a rigid short tube 52 that is connected to the sliding member 36, and a rigid long tube 54 that is connected to and extends through the sliding member 36. The illustrated short and long tubes are made of plastic and stainless steel, respectively. The long tube 54 is preferably molded into the sliding member 36, but could instead be inserted into the sliding member 36 after the sliding member 36 is formed. The long tube 54 provides operative connection between the interior of the arcuate member 46 and a terminal end 56 of the long tube 54, which ends about 9.0 mm beyond the end of the sliding member 36.

The terminal end 56 of the long tube 54 is designed to be interconnected with a source of fluid, such as saline solution stored in an IV bag (not shown). Alternatively, the source of fluid could be a fluid pump (not shown) that is selectively operated to provide fluid to the terminal end 56. As another option, a selectively operable valve (not shown) could be operatively positioned between a pressurized reservoir (not shown) and the terminal end 56, and the valve could be selectively opened and closed to deliver fluid to the terminal end 56 as desired.

An adhesive patch 58 is secured to the bottom surface of the base member 26. The adhesive patch 58 facilitates securement of the base member to the face of the patient. For example, the adhesive patch 58 can be engaged with the patient's cheek to secure the device 10 relative to the patient's eye 12. This feature allows the device to be used without the need for constant holding by medical personnel.

In operation, the sliding member 36 is initially positioned in the retracted position, and the engaging member 20 is engaged with the lower eyelid 16 by sliding the engaging member 20 under the lower eyelid 16 (FIG. 3). The raised portions 42 on the sliding member 36 are then engaged, and the fluid dispenser 44 is slid relative to the engaging member 20 toward the upper eyelid 14. The fluid dispenser 44 is then engaged with the upper eyelid 14 by sliding the fluid dispenser 44 under the upper eyelid 14 (FIG. 5). The fluid dispenser 44 is held in spaced relation relative to the engaging member 20 due to the frictional interaction between the sliding member 36 and the base member 26, thereby holding the eyelids separated. The adhesive patch is then engaged with the patient's cheek to hold the device stationary relative to the patient's eye. When fluid is to be provided to the eye 12, all that is required is that fluid be provided to the terminal end 56 of the long tube 54, such as by any of the techniques described above.

The fluid will be dispersed through the orifices 48 in an arcuately-shaped pattern, thereby simultaneously providing fluid at multiple locations on the eye 12. By virtue of the opening 50 in the fluid dispenser 44, the eye 12 can be visually and physically accessed, and the inner surface of the upper eyelid 14 is irrigated. The utilization of a wire for the engaging member 20 enhances irrigation of the inner surface of the lower eyelid 16. By virtue of the positioning of the orifices 48, the fluid will be provided under the eyelid, thereby ensuring proper irrigation and moisturization under the eyelid.

The foregoing description of the present invention has been presented for purposes of illustration and description. Furthermore, the description is not intended to limit the invention to the form disclosed herein. Consequently, variations and modifications commensurate with the above teachings, and the skill or knowledge of the relevant art, are within the scope of the present invention. The embodiments described herein are further intended to explain best modes known for practicing the invention and to enable others skilled in the art to utilize the invention in such, or other, embodiments and with various modifications required by the particular applications or uses of the present invention. It is intended that the appended claims be construed to include alternative embodiments to the extent permitted by the prior art.

What is claimed is:

1. An ocular irrigation device for use in holding opposing eyelids of an eye separated and providing irrigating fluid under at least one of the eyelids, said irrigation device comprising:

an engaging member engageable with at least one of the eyelids; and a fluid dispenser having at least one fluid-dispensing orifice, said fluid dispenser is arranged relative to said engaging member such that said orifice is positionable under at least one of the eyelids when the engaging member is engaging the opposing eyelid.

2. An ocular irrigation device as claimed in claim 1, wherein said engaging member comprises a wire formed into an arcuate portion, said arcuate portion being positionable under an eyelid.

3. An ocular irrigation device as claimed in claim 2, wherein said arcuate portion is round in cross section.

4. An ocular irrigation device as claimed in claim 1, wherein said fluid dispenser comprises a hollow tubular member with said orifice positioned in said tubular member.

5. An ocular irrigation device as claimed in claim 1, wherein said fluid dispenser includes an opening for allowing access to the eye when the orifice is positioned under the eyelid.

6. An ocular irrigation device comprising:

a fluid dispenser including an arcuate portion positionable under an eyelid of an eye, said arcuate portion including a plurality of orifices for dispensing fluid under the eyelid at multiple arcuately-spaced locations; and an engaging member connected to said fluid dispenser and engageable with the opposing eyelid.

7. An ocular irrigation device as claimed in claim 6, wherein said orifices are in an outer wall of said arcuate portion.

8. An ocular irrigation device as claimed in claim 6, wherein said arcuate portion is tubular in shape.

9. A method of irrigating an eye using a device having an engaging member and a fluid dispenser interconnected with the engaging member, said method comprising the steps of:

engaging the engaging member with one of the eyelids;

positioning the fluid dispenser under an opposing eyelid; and providing fluid through the fluid dispenser and directly under the opposing eyelid.

10. A method as claimed in claim 9, wherein said positioning step includes the step of holding the eyelids separated from each other.

11. A method as claimed in claim 9, further comprising the step of moving the fluid dispenser relative to the engaging member.

* * * * *